United States Patent [19]
Karassik et al.

[11] Patent Number: 5,925,338
[45] Date of Patent: Jul. 20, 1999

[54] CLEAR ANTIPERSPIRANT OR DEODORANT GEL COMPOSITION WITH VOLATILE LINEAR SILICONE TO REDUCE STAINING

[75] Inventors: Nancy M. Karassik, Concord; Philip P. Angelone, Jr., Wilmington; Patricia Riley Boyle, Stow; Patricia Di Domizio, Malden; Cheryl Weston Galante; Jay C. Patel, both of Braintree; Patricia A. Rogers, Hyde Park, all of Mass.

[73] Assignee: The Gillette Company, Boston, Mass.

[21] Appl. No.: 08/790,563

[22] Filed: Jan. 29, 1997

[51] Int. Cl.$^6$ .......................................... A61K 7/32
[52] U.S. Cl. .............................. 424/65; 424/401; 424/66; 424/67; 424/68; 514/63; 514/873; 514/944
[58] Field of Search ................................. 424/401, 65, 66, 424/67, 68; 514/63, 873, 944

[56] References Cited

U.S. PATENT DOCUMENTS

| | | | |
|---|---|---|---|
| 4,499,069 | 2/1985 | Krafton | 424/66 |
| 4,673,570 | 6/1987 | Soldati | 424/66 |
| 4,980,156 | 12/1990 | Raleigh et al. | 424/66 |
| 5,225,188 | 7/1993 | Abrutyn et al. | 424/66 |
| 5,456,906 | 10/1995 | Powell et al. | 424/65 |
| 5,480,637 | 1/1996 | Smith | 424/78.02 |
| 5,587,153 | 12/1996 | Angelone, Jr. et al. | 424/66 |
| 5,623,017 | 4/1997 | Hill | 524/860 |

FOREIGN PATENT DOCUMENTS

| | | |
|---|---|---|
| 0499 398 | 8/1992 | European Pat. Off. . |
| WO 96/06594 | 7/1996 | WIPO . |

*Primary Examiner*—Jose' G. Dees
*Assistant Examiner*—Michael A. Williamson
*Attorney, Agent, or Firm*—Stephan P. Williams

[57] ABSTRACT

The present invention is directed to a clear antiperspirant or deodorant gel composition which exhibits reduced staining while retaining excellent aethetic attributes and efficacy. The gel composition is a water-in-oil emulsion having a viscosity of about 50,000 to 250,000 cP, preferably about 100,000 to 200,000 cP. The water phase comprises about 75 to 90% of the composition and contains a deodorant or antiperspirant effective amount (e.g. about 3 to 25%) of an antiperspirant active dissolved therein. The oil phase comprises about 10 to 25% of the composition and contains a silicone oil and a polyether substituted silicone emulsifying agent. The silicone oil comprises a mixture of a non-volatile silicone, preferably a non-volatile linear silicone, and a volatile linear silicone. It has been found that reducing the amount of non-volatile silicone in the known gel composition to a relatively low level (e.g. below about 5%) and adding an amount of volatile linear silicone to the composition (e.g. above about 2%, preferably above about 5%) substantially improves the non-staining properties of the composition.

16 Claims, No Drawings

CLEAR ANTIPERSPIRANT OR DEODORANT GEL COMPOSITION WITH VOLATILE LINEAR SILICONE TO REDUCE STAINING

BACKGROUND OF THE INVENTION

This invention relates to clear antiperspirant and deodorant gel compositions. Clear antiperspirant and deodorant gel compositions are disclosed in U.S. Pat. No. 5,587,153, the disclosure of which is incorporated herein by reference. Such compositions are sold under the Gillette®, Right Guard®, Natrel® Plus, Dry Idea® and Soft & Dri® brand names. Such compositions are water-in-oil emulsions having a viscosity of about 50,000 to 250,000 cP, preferably about 100,000 to 200,000 cP. The water phase comprises about 75 to 90% of the composition and contains a deodorant or antiperspirant effective amount (e.g. about 3 to 25%) of an antiperspirant active. The oil phase comprises about 10 to 25% of the composition and contains a silicone oil and a polyether substituted silicone emulsifying agent. For optimum clarity the refractive index of the oil phase and the water phase should be matched to within about 0.001 or better, preferably to within about 0.0004.

While the above-described clear antiperspirant and deodorant gel compositions have been extraordinarily successful, they suffer from one particular disadvantage—staining of clothing that comes in contact with the underarm of the user. Accordingly, significant efforts have been made to try to reduce or eliminate fabric staining by altering the components of the composition. However, this objective has been difficult to achieve since any alteration in the composition tends to diminish the aesthetic attributes and/or efficacy of the product. Therefore, it is an object of the present invention to provide a clear antiperspirant or deodorant gel composition having reduced staining without any loss in efficacy or aesthetic attributes.

SUMMARY OF THE INVENTION

The present invention is directed to a clear antiperspirant or deodorant gel composition which exhibits reduced staining while retaining excellent aesthetic attributes and efficacy. The gel composition is a water-in-oil emulsion having a viscosity of about 50,000 to 250,000 cP, preferably about 100,000 to 200,000 cP, at 21° C. The water phase comprises about 75 to 90% of the composition and contains a deodorant or antiperspirant effective amount (e.g. about 3 to 25%) of an antiperspirant active dissolved therein. The oil phase comprises about 10 to 25% of the composition and contains a silicone oil and a polyether substituted silicone emulsifying agent. The silicone oil comprises a mixture of a non-volatile silicone, preferably a non-volatile linear silicone, and a volatile linear silicone. It has been found that reducing the amount of non-volatile silicone in the known gel composition to a relatively low level (e.g. below about 5%) and adding an amount of volatile linear silicone to the composition (e.g. above about 2%, preferably above about 5%) substantially improves the non-staining properties of the composition.

DETAILED DESCRIPTION OF THE INVENTION

The antiperspirant and deodorant gel compositions of the present invention are water-in-oil emulsions in which the water phase comprises about 75 to 90% of the composition. The water phase is primarily water and has an antiperspirant salt dissolved therein in an amount to achieve an antiperspirant or deodorant effect. The water phase may also include lower alkanols, such as ethanol, and/or polyhydric alcohols (typically of 3 to 6 carbon atoms), such as propylene glycol, dipropylene glycol or sorbitol. If included in the composition, the total amount of lower alkanol will generally comprise less than 15% of the composition, preferably 10% or less, by weight. The amount of polyhydric alcohol will fall within the range of about 4 to 35% of the composition by weight. The polyhydric alcohol may be advantageously utilized to adjust the refractive index of the water phase so that it matches the refractive index of the oil phase (preferably to within about 0.0004) in order to achieve maximum clarity of the final composition. The gel composition should have a clarity better than 100 NTU (Nephelometric Turbidity Units), preferably better than 75 NTU, and most preferably better than 50 NTU at 21° C.

Antiperspirant salts which may be used in the compositions of the present invention include any of the conventional aluminum, zirconium and aluminum-zirconium salts known to be useful in antiperspirant compositions. These salts include aluminum halides and aluminum hydroxy halides (e.g. aluminum chlorohydrate), and mixtures or complexes thereof with zirconyl oxyhalides and zirconyl hydroxyhalides (e.g. aluminum-zirconium chlorohydrate). The antiperspirant salts are utilized in solubilized form—i.e. they are dissolved in water, alcohol, polyhydric alcohol, aqueous alcohol, or aqueous polyhydric alcohol—when formulated into the gel compositions of the present invention. Preferably, the antiperspirant salts are utilized as aqueous solutions, typically of about 30 to 50% concentration. Most preferably, such solutions are not prepared by redissolving spray dried salts since spray dried salts have oxides which can cause cloudiness in the final composition.

Preferred aluminum salts are those having the general formula $Al_2(OH)_{6-a}X_a$ wherein X is Cl, Br, I or $NO_3$, and a is about 0.3 to about 4, preferably about 1 to 2, such that the Al to X mole ratio is about 1:1 to 2.1:1. These salts generally have some water of hydration associated with them, typically on the order of 1 to 6 moles per mole of salt. Most preferably, the aluminum salt is aluminum chlorohydrate (i.e. X is Cl) and a is about 1, such that the aluminum to chlorine mole ratio is about 1.9:1 to 2.1:1.

Preferred aluminum-zirconium salts are mixtures or complexes of the above-described aluminum salts with zirconium salts of the formula $ZrO(OH)_{2-pb}Y_b$ wherein Y is Cl, Br, I, $NO_3$, or $SO_4$, b is about 0.8 to 2, and p is the valence of Y. The zirconium salts also generally have some water of hydration associated with them, typically on the order of 1 to 7 moles per mole of salt. Preferably the zirconium salt is zirconyl hydroxychloride of the formula $ZrO(OH)_{2-b}Cl_b$ wherein b is about 1 to 2, preferably about 1.2 to about 1.9. The preferred aluminum-zirconium salts have an Al:Zr ratio of about 1.7 to about 12.5, most preferably about 2 to about 10, and a metal:X+Y ratio of about 0.73 to about 2.1, preferably about 0.9 to 1.5. A preferred salt is aluminum-zirconium chlorohydrate (i.e. X and Y are Cl), which has an Al:Zr ratio of about 2 to about 10 and a metal:Cl ratio of about 0.9 to about 2.1. Thus, the term aluminum-zirconium chlorohydrate is intended to include the tri-, tetra-, penta- and octa-chlorohydrate forms. The aluminum-zirconium salt complexes may also contain a neutral amino acid, preferably glycine, typically with a Gly:Zr ratio of about 1:1.

It may be desirable to utilize enhanced efficacy aluminum and aluminum-zirconium antiperspirant salts in the compositions of the present invention. By "enhanced efficacy antiperspirant salts" is meant antiperspirant salts which, when reconstituted as 10% aqueous solutions, produce an HPLC chromatogram (as described, for example, in U.S.

Pat. No. 5,330,751, which is incorporated herein by reference) wherein at least 70%, preferably at least 80%, of the aluminum is contained in two successive peaks, conveniently labeled peaks 3 and 4, wherein the ratio of the area under peak 4 to the area under peak 3 is at least 0.5, preferably at least 0,7, and most preferably at least 0.9 or higher. Any suitable HPLC technique may be employed provided that it is capable of resolving the Al component into five peaks. The enhanced efficacy (or activated) antiperspirant salts are well-known in the industry and are commercially available from several suppliers.

Sufficient antiperspirant salt should be added so that the final composition, after all components are added, includes between about 3% and about 30%, preferably about 6% to about 25%, of the antiperspirant salt by weight. Generally, the composition will be designated an antiperspirant composition if it contains sufficient antiperspirant salt to effectively inhibit perspiration. This amount of antiperspirant salt will typically be greater than about 10% by weight. Below that amount, the composition will generally be designated a deodorant composition. It should be noted that reference throughout this application to weight percent of antiperspirant salt is intended to be calculated in accordance with the standard industry method, which includes bound water and glycine. If the amount of antiperspirant salt is calculated in accordance with the recently adopted U.S.P. method, which excludes bound water and glycine, the range of suitable weight percents for inclusion in the composition will be somewhat lower than that stated above.

The oil phase comprises about 10 to 25% of the composition. Generally the oil phase comprises a silicone oil and/or other organic oil. The oil phase is the continuous phase and provides emolliency while reducing the wetness of the composition. The oil phase also includes a surfactant material which is effective in emulsifying the water phase into the oil phase. A preferred surfactant material is a polyether substituted silicone such as dimethicone copolyol. An especially preferred surfactant is DC 3225C (Dow Corning), which is a blend of cyclomethicone and dimethicone copolyol.

It has been found that the presence of significant quantities of non-volatile oils in the previously known gel compositions causes the compositions to stain clothing. Such non-volatile oils include non-volatile silicones, such as dimethicone (viscosity of about 10 cst or more), and other organic emollient oils such as octyl isononanoate. Such oils are normally included in the composition to provide emolliency and to prevent stickiness or tackiness in the final product. Heretofore, it has not been possible to reduce the non-volatile oil component from the gel composition without having an adverse effect on the aesthetic attributes of the product.

A critical component of the gel composition of the present invention is the addition of a volatile linear silicone to replace some or all of the non-volatile oil component. This volatile linear silicone is a polydimethylsiloxane or dimethicone which has a relatively low average molecular weight, a relatively low viscosity and a significant vapor pressure at 25° C. (i.e. one gram of fluid placed on No. 1 filter paper leaves substantially no visible residue after thirty minutes at room temperture). It also typically has a boiling point under 250° C. The volatile linear silicone (or volatile dimethicone) is represented by the formula $(CH_3)_3SiO(Si(CH_3)_2O)_nSi(CH_3)_3$ in which n is an integer of about 0 to about 6, preferably about 1 to about 4. One of the methyl groups of the foregoing formula may be replaced with an alkyl group (e.g. of 2 to 10 carbon atoms) to provide an alkylmethylsiloxane. Such material includes, for example, DC 2-1731 (Dow Corning), which is 3-hexylheptamethyltrisiloxane (viscosity=1.0 cst). While a pure silicone polymer may be utilized, generally the volatile linear silicone is a mixture of silicone polymers of the above formula. The volatile linear silicone will have a viscosity of less than about 5 cst (or less than about 5 cP), preferably between about 0.6 and 3.0 cst, more preferably between 1.0 and 2.0 cst. (For silicones with a specific gravity at 25° C. in the 0.75 to 0.92 range, the foregoing viscosity ranges convert to about 0.5 to 2.8 cP, preferably about 0.8 to 1.8 cP) Suitable volatile linear silicones include DM Fluid 0.65 cs (hexamethyldisiloxane), DM Fluid 1.0 cs (octamethyltrisiloxane), DM Fluid 1.5 cs, DM Fluid 2.0 cs (dodecamethylpentasiloxane), DC 2-1184 and DC 2-1731, all available from Dow Corning. DC 2-1184, which has a viscosity of about 1.7 cst and an average molecular weight of about 320 (i.e. n is about 1 to 3 in the above formula), is preferred.

The amount of volatile linear silicone to be incorporated into the composition may be varied depending on the nature of the particular volatile linear silicone utilized and the other oil components present in the composition. That is, one may balance the amount of volatile linear silicone and the amount of non-volatile oil in order to achieve the desired balance of non-staining versus non-stickiness or emolliency. Generally, the volatile linear silicone will be utilized in an amount of about 2 to 15%, preferably about 3 to 10% of the composition by weight.

The oil phase may also comprise a sufficient amount of a non-volatile emollient oil in order to provide the final composition with desirable application aesthetics, particularly emolliency and non-stickiness. Especially preferred is a non-volatile silicone, such as dimethicone (e.g. DC 225, available from Dow Corning). The composition may also contain a non-volatile organic oil (or a mixture of organic oils), which may be used alone or in combination with a non-volatile silicone. Generally, the final composition will comprise less than about 5% by weight of non-volatile oil. Preferably, the composition will comprise from 0 to 5%, most preferably about 1 to 4%, of non-volatile silicone by weight. In formulations containing low amounts of antiperspirant salt (i.e. about 10% or less), it may be possible and desirable to remove all of the non-volatile oil. In such a case, the silicone oil component may include only the volatile linear silicone and optionally a volatile cyclic silicone.

As mentioned previously, the oil phase also includes a surfactant material, the type and amount of which is selected to emulsify the water phase within the oil phase. Preferably, the surfactant material is a polyether substituted silicone such as dimethicone copolyol. Generally, the composition will comprise about 0.5 to 1.5% of dimethicone copolyol. Advantageously, the dimethicone copolyol may be added as a blend with cyclomethicone. A typical blend is DC 3225C (Dow Coming), which contains about 90% cyclomethicone (DC 344) by weight. If added as such a blend, then the cyclomethicone and dimethicone copolyol blend will comprise about 5 to 15%, preferably about 7 to 10%, of the composition by weight. The cyclomethicone also contributes to the overall application aesthetics of the product, such as dryness. Naturally, of course, a volatile cyclic silicone may be included in the composition of the present invention as a separate component, if desired. If separately added, the volatile cyclic silicone will generally comprise about 0 to 18%, preferably about 5 to 15%, of the composition by weight.

While the compositions of the present invention may be formulated and used with the above-described basic constituents, it may also be desirable to add other optional components to achieve desired application aesthetics or other effects. For example, it may be desired to include various ethoxylated and/or propoxylated fatty ethers, antimicrobial or deodorant active agents such as triclosan, fragrances, preservatives, chelating agents, etc.

The invention may be further described by the following examples which are for illustrative purposes only. All parts and percentages are by weight.

Examples 1 to 6

| Ingredient | Weight Percent | | | | | |
|---|---|---|---|---|---|---|
| | Ex. 1 | Ex. 2 | Ex. 3 | Ex. 4 | Ex. 5 | Ex. 6 |
| Water | 42.45 | 38.41 | 37.88 | 44.40 | 38.77 | 39.81 |
| Al—Zr Tetrachlorohydrate-Gly[1] | 23.50 | 23.50 | 23.50 | 23.50 | 6.00 | 23.50 |
| Propylene Glycol | 5.85 | 5.89 | 15.55 | 5.90 | 34.68 | 8.69 |
| Ethanol | 10.00 | 14.00 | 5.00 | 8.00 | | 10.00 |
| Volatile Dimethicone[2] | 7.00 | 7.00 | 5.22 | | 3.00 | |
| Volatile Dimethicone[3] | | | | 5.10 | | |
| Volatile Dimethicone[4] | | | | | | 4.72 |
| Dimethicone[5] | 3.00 | 3.00 | | 4.90 | | |
| Dimethicone Copolyol[6] | 8.00 | 8.00 | 8.10 | 8.00 | 9.00 | 8.10 |
| Cyclomethicone (D-5) | | | | | 7.00 | 5.00 |
| Octyl Isononanoate | | | 4.50 | | | |
| Preservative | | | | | 1.15 | |
| Fragrance | 0.20 | 0.20 | 0.25 | 0.20 | 0.40 | 0.18 |

[1]Added as 50% aqueous solution. 23.5% (std. industry method) ≅ 18% salt (U.S.P.).
[2]DC 2-1184 (Dow Corning). Blend of linear polydimethylsiloxanes (Avg. MW ≅ 320; viscosity ≅ 1.7 cst)
[3]DC 0.65 cs 200 Fluid (Dow Corning). Hexamethyldisiloxane (MW = 162; viscosity = 0.65 cst)
[4]DC 2-1731 (Dow Corning). 3-hexylheptamethyltrisiloxane (MW = 306; viscosity = 1.0 cst)
[5]DC-225 (Dow Corning). Non-volatile linear polydimethylsiloxane (Avg. MW ≅ 1000; viscosity ≅ 9.5 cst)
[6]DC-3225C (Dow Corning). Blend of cyclomethicone (90% DC 344) and polyether substituted dimethicone (10% dimethicone copolyol)

The above compositions were made in the following manner. The water phase components and the oil phase components are each mixed in separate containers and filtered and the refractive index of each is measured. The refractive index of the water phase is adjusted to match the refractive index of the oil phase to within 0.0004 by addition of water or propylene glycol as required. The water phase is then slowly added to the oil phase at about 18° C. with sufficient mixing to form a clear emulsion with minimum aeration. This emulsion is then sheared to form a clear gel with a viscosity of about 130,000 to 160,000 cP.

The product of Example 1 was compared to Gillette® Series Clear Gel Antiperspirant, which has a similar formulation but contains 9.7% dimethicone (non-volatile) and no volatile linear silicone. The two products were tested for thermal efficacy (i.e. hot room sweat reduction), application aesthetics (i.e. overall preference, stickiness, greasiness, wetness, odor protection, perspiration protection, white residue, etc.) and fabric staining in separate panel studies involving 34 to 56 male panelists (AvB; test product applied to one axilla and control product applied to other axilla). The test product (Ex. 1) exhibited no significant difference in thermal efficacy or application aesthetics versus the control. However, the test product exhibited a significant reduction in fabric staining versus the control. The products of Examples 2 to 6 also exhibit reduced staining.

Fabric staining was measured in the following manner. Each panelist was assigned a fresh white cotton T-shirt at the beginning of the study. The T-shirt was worn by the panelist for about seven hours each day for twenty days, after first washing the axillae then applying about 0.8 grams of product. The shirts were laundered and dried at the end of each day. Staining (or yellowing) was measured in two ways. A visual rating was assigned to each shirt underarm by two trained judges using a scale of 0 to 5, with 0 being none and 5 being severe, then the scores were averaged. Staining was also measured by taking three light reflectance readings (Minolta® Chroma Meter CR-310) from each shirt underarm and comparing that average to the average of three readings taken from the back of the shirt (control).

While particular embodiments of the invention have been shown and described for illustrative purposes, it will be apparent to those skilled in the art that various changes and modifications may be made without departing from the spirit and scope of the invention, which is defined by the claims which follow.

What is claimed is:

1. A clear gel composition comprising a water-in-oil emulsion having a viscosity of about 50,000 to 250,000 cP at 21° C., wherein the water phase comprises about 75 to 90% by weight of said emulsion and has about 3 to 25% by weight of an antiperspirant salt dissolved therein, and wherein the oil phase comprises about 10 to 25% by weight of said emulsion and includes a volatile cyclic silicone, a polyether substituted silicone emulsifying agent, 0 to about 5% by weight of a non-volatile oil and about 2 to 15% by weight of a volatile linear silicone.

2. The composition of claim 1 wherein the oil phase comprises about 3 to 10% by weight of said volatile linear silicone.

3. The composition of claim 2 wherein said non-volatile oil comprises a silicone oil.

4. The composition of claim 3 wherein said non-volatile oil comprises a dimethicone.

5. The composition of claim 2 wherein said non-volatile oil comprises an organic oil.

6. The composition of claim 5 wherein said non-volatile oil comprises octyl isononanoate.

7. The composition of claim 1, 2, 3, 4, 5 or 6 wherein the volatile linear silicone comprises one or more polydimethylsiloxanes of the formula

$(CH_3)_3SiO(Si(CH_3)_2O)_nSi(CH_3)_3$ in which n is an integer between 0 and 6.

8. The composition of claim 1, 2, 3, 4, 5 or 6 wherein the volatile linear silicone comprises one or more polydimethylsiloxanes of the formula

$(CH_3)_3SiO(Si(CH_3)_2O)_nSi(CH_3)_3$ in which n is an integer between 1 and 4.

9. The composition of claim 1 wherein the volatile linear silicone has a viscosity of about 0.6 to about 3.0 cst.

10. The composition of claim 7 wherein the volatile linear silicone has a viscosity of about 0.6 to about 3.0 cst.

11. The composition of claim 1 wherein the volatile linear silicone has a viscosity of about 1.0 to about 2.0 cst.

12. The composition of claim 8 wherein the volatile linear silicone has a viscosity of about 1.0 to about 2.0 cst.

13. The composition of claim 1 wherein the water phase additionally comprises a lower alkanol and/or a polyhydric alcohol.

14. The composition of claim 13 wherein the lower alkanol is ethanol and the polyhydric alcohol is propylene glycol.

15. The composition of claim 1 wherein the polyether substituted silicone emulsifying agent comprises a dimethicone copolyol.

16. The composition of claim 7 wherein the polyether substituted silicone emulsifying agent comprises a dimethicone copolyol.

* * * * *